United States Patent
Seve et al.

(10) Patent No.: US 9,568,482 B2
(45) Date of Patent: Feb. 14, 2017

(54) ANTIBODIES SPECIFIC FOR ZNT8

(75) Inventors: Michel Seve, Grenoble (FR); Alain Favier, Bernin (FR)

(73) Assignees: COMMISSARIAT A L'ENERGIE ATOMIQUE, Paris (FR); UNIVERSITE JOSEPH FOURIER, Grenoble (FR)

(*) Notice: Subject to any disclaimer, the term of this patent is extended or adjusted under 35 U.S.C. 154(b) by 1335 days.

(21) Appl. No.: 12/907,695

(22) Filed: Oct. 19, 2010

(65) Prior Publication Data

US 2011/0027807 A1 Feb. 3, 2011

Related U.S. Application Data

(62) Division of application No. 10/535,395, filed as application No. PCT/FR03/03413 on Nov. 18, 2003, now Pat. No. 7,851,164.

(30) Foreign Application Priority Data

Nov. 18, 2002 (FR) .................... 02 14374

(51) Int. Cl.
| | |
|---|---|
| *G01N 33/68* | (2006.01) |
| *C07K 14/705* | (2006.01) |
| *C07K 16/28* | (2006.01) |
| *C12Q 1/68* | (2006.01) |
| *A61K 38/00* | (2006.01) |

(52) U.S. Cl.
CPC ......... *G01N 33/6872* (2013.01); *C07K 14/705* (2013.01); *C07K 16/28* (2013.01); *C12Q 1/6883* (2013.01); *A01K 2217/05* (2013.01); *A61K 38/00* (2013.01); *C07K 2317/34* (2013.01); *C12Q 2600/158* (2013.01); *G01N 2500/04* (2013.01); *G01N 2500/10* (2013.01)

(58) Field of Classification Search
None
See application file for complete search history.

(56) References Cited

FOREIGN PATENT DOCUMENTS

| WO | 01/42789 | 6/2001 |
|---|---|---|
| WO | 02/24733 | 3/2002 |

OTHER PUBLICATIONS

Melton D. et al.: "*Homo sapiens* cDNA clone Image: 5779491 5' similar to TR:Q62941 zinc transporter ZNT-2; mRNA sequence" Database EMBL 'Online! ik02a02.y1 Human insulinoma, May 9, 2002. XP002246606.
Melton D. et al.: "*Homo sapiens* cDNA clone Image: 5782969 5' similar to TR: Q62941 zinc transporter ZNT-2; mRNA sequence" Database EMBL 'Online! ik36b01.y1 HR85 islet., May 28, 2002, XP002246607, May 28, 2002.
Melton D. et al.: "*Homo sapiens* cDNA clone Image: 5782969 5' similar to TR: Q62941 Zinc transporter ZNT-2; mRNA sequence" Database EMBL Online! in61h03.y1 HR85 islet. XP002246608, Oct. 24, 2002.
Tomita T: "New markers for pancreatic islets and islet cell tumors" Pathology International 2002 Japan, vol. 52, No. 7, pp. 425-432, 2002. XP002246605.

*Primary Examiner* — Gerald R Ewoldt
(74) *Attorney, Agent, or Firm* — Oblon, McClelland, Maier & Neustadt, L.L.P.

(57) ABSTRACT

Provided are antibodies specific for ZnT8. In particular, provided are monoclonal or polyclonal non-naturally occurring antibodies which specifically recognizes an epitope selected from the group consisting of SEQ ID NO. 7, SEQ ID NO. 8, SEQ ID NO. 9 and SEQ ID NO. 10 as described herein.

8 Claims, 4 Drawing Sheets

SEQUENCE LISTING

```
<160> NUMBER OF SEQ ID NOS: 10

<210> SEQ ID NO 1
<211> LENGTH: 1110
<212> TYPE: DNA
<213> ORGANISM: Homo sapiens

<400> SEQUENCE: 1
atggagtttc ttgaaagaac gtatcttgtg aatgataaag ctgccaagat gcatgctttc      60
acactagaaa gtgtggaact ccaacagaaa ccggtgaata aagatcagtg tcccagagag     120
agaccagagg agctggagtc aggaggcatg taccactgcc acagtggctc caagcccaca     180
```

```
gaaaaggggg cgaatgagta cgcctatgcc aagtggaaac tctgttctgc ttcagcaata    240
tgcttcattt tcatgattgc agaggtcgtg ggtgggcaca ttgctgggag tcttgctgtt    300
gtcacagatg ctgcccacct cttaattgac ctgaccagtt tcctgctcag tctcttctcc    360
ctgtggctgt catcgaagcc tccctctaag cggctgacat ttggatggca ccgagcagag    420
atccttggtg ccctgctctc catcctgtgc atctgggtgg tgactggcgt gctagtgtac    480
ctggcatgtg agcgcctgct gtatcctgat taccagatcc aggcgactgt gatgatcatc    540
gtttccagct gcgcagtggc ggccaacatt gtactaactg tggttttgca ccagagatgc    600
cttggccaca atcacaagga agtacaagcc aatgccagcg tcagagctgc ttttgtgcat    660
gcccttggag atctatttca gagtatcagt gtgctaatta gtgcacttat tatctacttt    720
aagccagagt ataaaatagc cgacccaatc tgcacattca tcttttccat cctggtcttg    780
gccagcacca tcactatctt aaaggacttc tccatcttac tcatggaagg tgtgccaaag    840
agcctgaatt acagtggtgt gaaagagctt attttagcag tcgacggggt gctgtctgtg    900
cacagcctgc acatctggtc tctaacaatg aatcaagtaa ttctctcagc tcatgttgct    960
acagcagcca gccgggacag ccaagtggtt cggagagaaa ttgctaaagc ccttagcaaa   1020
agctttacga tgcactcact caccattcag atggaatctc cagttgacca ggaccccgac   1080
tgccttttct gtgaagaccc ctgtgactag                                    1110
```

<210> SEQ ID NO 2
<211> LENGTH: 369
<212> TYPE: PRT
<213> ORGANISM: Homo sapiens

<400> SEQUENCE: 2

Met Glu Phe Leu Glu Arg Thr Tyr Leu Val Asn Asp Lys Ala Ala Lys
1               5                   10                  15

Met His Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Ala Ser Ala Ile
65                  70                  75                  80

Cys Phe Ile Phe Met Ile Ala Glu Val Val Gly Gly His Ile Ala Gly
                85                  90                  95

Ser Leu Ala Val Val Thr Asp Ala Ala His Leu Leu Ile Asp Leu Thr
            100                 105                 110

Ser Phe Leu Leu Ser Leu Phe Ser Leu Trp Leu Ser Lys Pro Pro
            115                 120                 125

Ser Lys Arg Leu Thr Phe Gly Trp His Arg Ala Glu Ile Leu Gly Ala
        130                 135                 140

Leu Leu Ser Ile Leu Cys Ile Trp Val Val Thr Gly Val Leu Val Tyr
145                 150                 155                 160

Leu Ala Cys Glu Arg Leu Leu Tyr Pro Asp Tyr Gln Ile Gln Ala Thr
                165                 170                 175

Val Met Ile Ile Val Ser Ser Cys Ala Val Ala Ala Asn Ile Val Leu
            180                 185                 190

Thr Val Val Leu His Gln Arg Cys Leu Gly His Asn His Lys Glu Val
        195                 200                 205

```
Gln Ala Asn Ala Ser Val Arg Ala Ala Phe Val His Ala Leu Gly Asp
    210                 215                 220

Leu Phe Gln Ser Ile Ser Val Leu Ile Ser Ala Leu Ile Ile Tyr Phe
225                 230                 235                 240

Lys Pro Glu Tyr Lys Ile Ala Asp Pro Ile Cys Thr Phe Ile Phe Ser
                245                 250                 255

Ile Leu Val Leu Ala Ser Thr Ile Thr Ile Leu Lys Asp Phe Ser Ile
            260                 265                 270

Leu Leu Met Glu Gly Val Pro Lys Ser Leu Asn Tyr Ser Gly Val Lys
        275                 280                 285

Glu Leu Ile Leu Ala Val Asp Gly Val Leu Ser Val His Ser Leu His
    290                 295                 300

Ile Trp Ser Leu Thr Met Asn Gln Val Ile Leu Ser Ala His Val Ala
305                 310                 315                 320

Thr Ala Ala Ser Arg Asp Ser Gln Val Val Arg Arg Glu Ile Ala Lys
                325                 330                 335

Ala Leu Ser Lys Ser Phe Thr Met His Ser Leu Thr Ile Gln Met Glu
            340                 345                 350

Ser Pro Val Asp Gln Asp Pro Asp Cys Leu Phe Cys Glu Asp Pro Cys
        355                 360                 365

Asp

<210> SEQ ID NO 3
<211> LENGTH: 24
<212> TYPE: DNA
<213> ORGANISM: Artificial sequence
<220> FEATURE:
<223> OTHER INFORMATION: Primer

<400> SEQUENCE: 3
gatgctgccc acctcttaat tgac                                          24

<210> SEQ ID NO 4
<211> LENGTH: 24
<212> TYPE: DNA
<213> ORGANISM: Artificial sequence
<220> FEATURE:
<223> OTHER INFORMATION: Primer

<400> SEQUENCE: 4
tcatcttttc catcctggtc ttgg                                          24

<210> SEQ ID NO 5
<211> LENGTH: 31
<212> TYPE: DNA
<213> ORGANISM: Artificial sequence
<220> FEATURE:
<223> OTHER INFORMATION: Primer

<400> SEQUENCE: 5
actctagaat ggagtttctt gaaagaacgt a                                  31

<210> SEQ ID NO 6
<211> LENGTH: 28
<212> TYPE: DNA
<213> ORGANISM: Artificial sequence
<220> FEATURE:
<223> OTHER INFORMATION: Primer

<400> SEQUENCE: 6
aatctagagt cacaggggtc ttcacaga                                      28
```

```
<210> SEQ ID NO 7
<211> LENGTH: 16
<212> TYPE: PRT
<213> ORGANISM: Homo sapiens

<400> SEQUENCE: 7

His Ile Ala Gly Ser Leu Ala Val Val Thr Asp Ala Ala His Leu Leu
1               5                   10                  15

<210> SEQ ID NO 8
<211> LENGTH: 15
<212> TYPE: PRT
<213> ORGANISM: Homo sapiens

<400> SEQUENCE: 8

Cys Glu Arg Leu Leu Tyr Pro Asp Tyr Gln Ile Gln Ala Thr Val
1               5                   10                  15

<210> SEQ ID NO 9
<211> LENGTH: 16
<212> TYPE: PRT
<213> ORGANISM: Homo sapiens

<400> SEQUENCE: 9

Cys Leu Gly His Asn His Lys Glu Val Gln Ala Asn Ala Ser Val Arg
1               5                   10                  15

<210> SEQ ID NO 10
<211> LENGTH: 13
<212> TYPE: PRT
<213> ORGANISM: Homo sapiens

<400> SEQUENCE: 10

Tyr Phe Lys Pro Glu Tyr Lys Ile Ala Asp Pro Ile Cys
1               5                   10
```

ANTIBODIES SPECIFIC FOR ZNT8

The present invention relates to a protein, called ZnT-8, that is expressed specifically in the pancreatic beta cells in islets of Langerhans, to the polynucleotide encoding said protein that is involved in the maturation and exocytosis of insulin, and also to applications thereof in particular for sorting and studying beta cells and for screening for medicinal products that act on diabetes and hyperinsulinism.

Diabetes is one of the most common diseases, affecting 5% of the population in industrialized countries, and constantly on the increase in all countries worldwide (prediction: 300 million in 2025, including 2.4 million in France). Among the various forms of diabetes, type I diabetes, or insulin-dependent diabetes, affects approximately 500 000 to 1 million individuals in the United States and 150 000 in France, i.e. 0.2 to 0.4% of the population. Characteristic symptoms comprise a high level of sugar in the blood and in the urine, considerable diuresis, intense hunger and thirst, and also weight loss.

Non-insulin dependent type II diabetes (NIDD), also described as "fat" diabetes or late-onset diabetes, often occurs around the age of about 50. It is treated by means of a diet, the taking of oral medicinal products, and insulin, after a few years of progression. Today, 2 million French people are treated with antidiabetic medicinal products and/or insulin.

Although diabetes can be controlled with insulin injections and controlled intake of carbohydrates, the complications associated with this pathology require, nowadays, novel approaches in terms of the prevention, treatment and diagnosis thereof.

The pancreas comprises two structures that are both morphologically and physiologically different:
- the exocrine pancreas, which produces the enzymes involved in digestion (amylase, lipase, etc.) and sodium bicarbonate;
- the endocrine pancreas, which produces the hormones involved in the control of blood glucose (insulin, glucagon, somatostatin and pancreatic polypeptide).

The cells of the endocrine pancreas are organized as microorgans dispersed in the pancreas in the form of islets (islets of Langerhans or pancreatic islets). Each pancreatic islet is made up of 4 cell types: alpha cells, beta cells, delta cells and PP cells. The alpha cells are located at the periphery of the islet and secrete glucagon. The beta cells are found at the center of the islet and are the only cells capable of secreting insulin in response to glucose. The delta cells are at the periphery and secrete somatostatin. The function of the PP cells is more controversial (synthesis of pancreatic polypeptide).

The lack of a cellular model for studying the beta cells, and also the lack of reliable and effective means of cell sorting suitable for this type of cell hinder the study of its function and therefore the development of novel methods of treatment of type I and II diabetes.

Among the treatments for diabetes, besides the regular administration of insulin, one of the approaches for the physiological control of glycemia and for normalization of glycemia in diabetics is to restore insulin secretion in vivo from cells. In this perspective, several solutions have been proposed:
- the obtaining of insulin-producing cells in animals in order to perform xenotransplantation;
- in vitro differentiation into insulin-secreting cells using isolated stem cells, with the aim of reimplantation [1], in order to bypass the problems of immunity and the need for immunosuppressive treatment in the patient. However, the production, at low cost, of large amounts of cells that produce insulin, by differentiation of stem cells, requires novel biomolecular tools that are in particular useful for the phenotyping and the purification of the differentiated cells;
- transplantation of pancreatic islets; the subject of many studies has recently been the preparation of pancreatic islets or beta cells for therapeutic purposes. The first step in the transplantation is the removal of the pancreas from a donor in whom brain death has been declared. The isolation of the islets begins with enzymatic digestion of the pancreas by means of a collagenase solution. Not all transplants require the digested islets to be purified. However, most researchers are today in agreement that purification of the islets is necessary for allotransplantation [2]. The islets are then transplanted, as a sufficient mass (minimum of 3000 IEQ/kg) by intraportal injection (IEQ: islet equivalent).

However, the isolation of pancreatic islets or beta cells requires specific and reliable means for selecting and identifying the beta cells.

Prior studies have attempted to develop methods for labeling beta cells. Mention may be made of:
- labeling with GFP (green fluorescent protein), which allows fluorescent labeling of the cells. The major drawback of this technique is the need to introduce an exogenous gene, or transgene, into the cell, what is more, using a viral vector (adenovirus) [1];
- the technique based on the considerable autofluorescence of the beta cell [2]. However, this technique lacks specificity with respect to the cell type;
- incubation of the cells with a zinc-specific fluorochrome: Newport Green [3] or dithizone [4]. This technique is based on the considerable zinc content of the beta cell. Zinc is a substantial constituent of insulin secretory granules and, in addition, plays a role in the control of this secretion [5]. However, these techniques have many drawbacks: use of a chemical product, risk of toxicity with respect to the beta cell, lack of specificity with respect to the cell type. In addition, dithizone poses a problem of rapid photodegradation [6];
- indirect demonstration by recognition, by a T-cell clone (WO 91/17186), of an antigen expressed by beta cells. The initial studies on this antigen provided no results in terms of characterization of the peptide sequence nor in terms of selectivity for the beta cell relative to the other cell types of the islet, but also of the pancreas or of the organism. More recent studies by the same authors show a much broader distribution of this antigen, which, as a result, is not specific for the beta cell [7].

Consequently, there is a lack of specific and reliable markers for the beta cell of pancreatic islets of Langerhans.

One of the aims of the present invention is to provide such a marker.

Islets of Langerhans accumulate very large amounts of zinc and therefore require a very effective and very specialized transporter in order to accumulate this zinc in the secretory vesicles [8]. Insulin, produced and stored in the pancreatic beta cell, is released into the extracellular medium by exocytosis in response to external stimuli, such as an increase in glucose concentration. This increase in glucose brings about a modification of the ATP/ADP ratio, the closing of potassium channels and the opening of calcium channels, which brings about exocytosis [9].

It is known that, in the presence of zinc, insulin can form tetramers and hexamers that bind the zinc in an insulin:zinc ratio of 4:1 and 6:2, respectively. The insulin is stored in the secretory granules in the form of a solid made up of hexamers attached to 2 zinc atoms per hexamer. The vesicles contain zinc in an excess of 1 to 1.5 times the amount necessary to form the insulin-zinc hexamers. During the exocytosis of insulin, the insulin-rich vesicles fuse with the plasma membrane of the beta cell and release the insulin, but also the zinc, into the circulation. The released zinc acts in a negative-feedback loop on the potassium channels, causing its activation and the arrest of exocytosis.

In mammalian cells, 7 homologous proteins having a zinc transporter function, called ZnT-1, -2, -3, -4, -5, -6 and -7, have been cloned and characterized. Analysis of the primary structure of these proteins has made it possible to define a common structural unit made up of 6 transmembrane domains and one histidine-rich intracellular loop. ZnT-1 is a ubiquitous transporter located in the plasma membrane, which ensures zinc efflux out of the cell [11]. ZnT-2 allows the cell to tolerate an excess of zinc in the culture medium, thus conferring zinc resistance by localizing it in acidic intracytoplasmic vesicles, thus ensuring an accumulation of the zinc in the cell that is well above the normal [12]. ZnT-3 and ZnT-4, that have been cloned in humans, have functions similar to ZnT-2. ZnT-3 is specific for certain tissues and is strongly expressed in the brain, in zinc-rich synaptic vesicle membranes, in hippocampal mossy fibers and in the testes. ZnT-4 is expressed ubiquitously, but high levels are found in the brain and the epithelial cells. This transporter is essential in the mammary epithelium, where it participates in the control of the zinc content of maternal milk. ZnT-5 and ZnT-6 are also ubiquitous transporters located in the Golgi apparatus. ZnT-7 is a ubiquitous transporter located specifically in the endoplasmic reticulum cells.

Previous studies mention an attempt to search for genes involved in zinc metabolism in the pancreatic beta cell. These studies did not result in the demonstration of a specific protein or transporter [10].

The inventors have isolated a 1110 base pair polynucleotide (SEQ ID NO. 1) representing the cDNA corresponding to an mRNA expressed specifically in the islet of Langerhans, and more particularly in the insulin-secreting cell or beta cell.

The polynucleotide of the invention encodes a protein called ZnT-8 (SEQ ID NO. 2), which protein of 369 amino acids, corresponding to an estimated molecular mass of 40.8 KDa, has a primary structure homologous to that of the proteins of the ZnT family. The gene encoding said protein is called ZnT-8.

The study of the transmembrane potential of the complete ZnT-8 protein shows that it has 6 transmembrane domains (amino acids 74-95, 107-126, 141-163, 177-196, 216-240, and 246-267), the N- and C-terminal ends being located in the cytoplasm. This study also shows that the secondary structure of this protein has 3 extracellular amino acid loops (amino acids 96-106, 164-176, and 241-245).

In addition, the location of the ZnT-8 protein in the insulin secretory vesicles and on the plasma membrane indicate that it is involved in zinc accumulation in the vesicles containing insulin, and therefore plays a role in the maturation and exocytosis of insulin in the beta cells of the pancreatic islets of Langerhans.

The ZnT-8 protein and the corresponding polynucleotide constitute, for the first time, a specific and reliable marker for the beta cell of the pancreatic islets of Langerhans; the uses of this marker are in particular as follows:

cell sorting; the marker makes it possible to envison selective sorting and detecting of beta cells, without chemical or biological modification of said cells, in particular using antibodies directed against said protein.

in vitro study model; the marker can be used in vitro for studying: (i) overexpression of the transporter (ZnT-8) in model cell lines (INS-1 rat insulinoma for example) and the impact on insulin secretion in response to a stimulation with glucose, (ii) sensitivity of the cells to cell death (apoptosis) induced by conditions of oxidative stress or of low or high zinc concentration, and (iii) the steps of differentiation of stem cells into insulin-secreting cells in response to various exogenous stimulations (growth factors, pancreatic extracts).

screening for medicinal products: the marker also represents a useful pharmacological target for screening for substances capable of modulating the expression of the ZnT-8 gene and/or the activity of the ZnT-8 protein, that can potentially be used for the treatment of diabetes and of hyperinsulinism.

diabetes diagnosis: the polynucleotide can also advantageously be used in the early diagnosis of diabetes in families at risk, in particular in that it makes it possible to detect observable mutations in the ZnT-8 gene and also to decrease or even eliminate the examinations usually carried out.

Thus, a subject of the present invention is the use, as a specific marker for the beta cells of pancreatic islets of Langerhans, of at least one isolated polynucleotide or of the corresponding protein, chosen from:

the polynucleotides comprising or having one of the following sequences: (a) the sequence SEQ ID NO. 1, (b) a fragment of the sequence SEQ ID NO. 1 of at least 15 consecutive nucleotides, preferably 20 nucleotides, even more preferably 25 to 30 nucleotides, (c) a sequence exhibiting a percentage identity of at least 80%, after optimal alignment, with one of the sequences defined in (a) or in (b), and (d) a sense or antisense sequence complementary to one of the sequences defined in (a), (b) or (c), and the proteins encoded by the polynucleotides as defined in (a), (b), (c) or (d) above, comprising or having one of the following sequences: (e) the sequence SEQ ID NO. 2, (f) a fragment of the sequence SEQ ID NO. 2 of at least 15 consecutive amino acids, (g) a sequence exhibiting a percentage identity of at least 60%, after optimal alignment, with one of the sequences defined in (e) or in (f) or at least 65% similarity, preferably 80% identity or at least 90% similarity, or even more preferably 90% identity or at least 95% similarity.

The invention encompasses the uses of the ZnT-8 protein and of the corresponding polynucleotide as defined above.

The polynucleotide as defined above can be isolated from Langerhans cells or from cellular DNA libraries, particularly from pancreatic cell DNA libraries, very particularly from a human pancreatic cell DNA library. Preferably, the cells used are islets of Langerhans cells.

The polynucleotide as defined above can also be obtained by a polymerase chain reaction (PCR) carried out on the total DNA of the Langerhans cells, by RT-PCR carried out on the total RNA of the beta cells of pancreatic islets of Langerhans, or by chemical synthesis.

For the purpose of the present invention, the following definitions apply.

The term "polynucleotide" is intended to mean a precise series of modified or unmodified nucleotides, possibly comprising non-natural nucleotides. Thus, this term covers any sequence which encodes a ZnT-8 protein or a fragment of said protein (genomic DNA, mRNA, cDNA), but also the corresponding sense or antisense oligonucleotides and the corresponding small interfering RNAs (siRNAs).

The expression "nucleic acids or proteins exhibiting a percentage identity, after optimal alignment, with a reference sequence" is intended to denote the nucleic acids or the proteins that exhibit, relative to the reference sequence, certain modifications, such as in particular a deletion, a truncation, an extension, a chimeric fusion and/or a substitution, in particular a point substitution, and for which the nucleotide sequence exhibits at least 80% identity and the amino acid sequence exhibits at least 65% identity, after optimal alignment, with the reference nucleotide or amino acid sequence.

The term "percentage identity" between two sequences (nucleic acid or protein sequences) is intended to denote a percentage of nucleotides or of amino acid residues that are identical between the two sequences to be compared, obtained after best alignment, this percentage being purely statistical and the differences between the two sequences being distributed randomly and over their entire length.

The term "best alignment" or "optimal alignment" is intended to denote the alignment for which the percentage identity determined as described hereinafter is the highest. Comparisons between two nucleotide or amino acid sequences are conventionally carried out: by comparing these sequences after having optimally aligned them, said comparison being carried out by segment or by "window of comparison" so as to identify and compare local regions of sequence similarity. The optimal alignment of the sequences for the comparison can be carried out in particular using one of the following algorithms: the local homology algorithm of Smith and Waterman (1981), the local homology algorithm of Neddleman and Wunsch (1970), the similarity search method of Pearson and Lipman (1988), the computer programs using these algorithms (GAP, BESTFIT, BLAST P, BLAST N, BLASTX, TBLASTX, FASTA and TFASTA in the Wisconsin Genetics Software Package (Genetics Computer Group, 575 Science Dr., Madison, Wis.) or on internet servers, in particular those of the National Center for Biotechnology Information (hypertext transfer protocol available on the worldwide web at ncbi.nlm.nih.gov), of the EMBL (hypertext transfer protocol available on the worldwide web at embl.org) and of the Ensembl project (hypertext transfer protocol available on the worldwide web at ensembl.org)).

In order to obtain the optimal alignment, the BLAST program is preferably used with the BLOSUM 62 matrix. The PAM or PAM250 matrices can also be used, as can an identity matrix for nucleotide sequences.

In order to obtain a "specific hybridization", high stringency hybridization conditions are preferably used, i.e. conditions of temperature and of ionic strength chosen such that they allow the specific and selective hybridization between complementary polynucleotides to be maintained.

By way of illustration, high stringency conditions in the hybridization step for the purposes of defining the polynucleotides described above are advantageously as follows: the DNA-DNA or DNA-RNA hybridization is carried out in two steps: (1) pre-hybridization at 42° C. for 3 hours in phosphate buffer (20 mM, pH 7.5) containing 5×SSC (1×SSC corresponds to a solution of 0.15 M NaCl+0.015 M sodium citrate), 50% of formamide, 7% of sodium dodecyl sulfate (SDS), 10×Denhardt's, 5% of dextran sulfate and 1% of salmon sperm DNA; (2) hybridization per se, for 20 hours at a temperature that depends on the length of the probe (i.e.: 42° C. for a probe longer than 100 nucleotides), followed by 2 washes of 20 minutes at 20° C. in 2×SSC+2% SDS, 1 wash of 20 minutes at 20° C. in 0.1×SSC+0.1% SDS. The final wash is carried out in 0.1×SSC+0.1% SDS for 30 minutes at 60° C., for a probe longer than 100 nucleotides. The high stringency hybridization conditions described above for a probe of defined length can be adjusted, by those skilled in the art, for longer or shorter probes.

The expression "suitable techniques or methods" is here intended to refer to the well-known techniques or methods conventionally used by those skilled in the art and disclosed in many works, such as in particular that entitled Molecular Cloning. A Laboratory Manual (Sambrook J, Russell D W. (2000) Cold Spring Harbor Laboratory Press) [13].

The polynucleotide as defined in c) exhibits a percentage identity of at least 80%, after optimal alignment, with a sequence as defined in a) or b), preferably 90%, more preferably 95%, even more preferably 98%. The polynucleotide as defined in c) includes the polynucleotides that are variants of the sequence SEQ ID NO. 1, i.e. all the polynucleotides corresponding to allelic variants, i.e. to individual variations in the sequence SEQ ID NO. 1. These natural variant sequences correspond to polymorphisms present in mammals, in particular in humans, and especially to polymorphisms that can lead to the occurrence of a pathology, for example cell death in the islets of Langerhans, and diabetes.

The term "variant polynucleotide" is also intended to denote any RNA or cDNA resulting from a mutation and/or from a variation of a splice site of the genomic sequence whose mRNA has the polynucleotide of sequence SEQ ID NO. 1 as its complementary DNA.

The similarity of a protein relative to a reference protein is assessed according to the percentage of amino acid residues that are identical or that differ by conservative substitutions, when the two sequences are aligned so as to obtain the maximum correspondence between them. For the purpose of the present invention, the term "conservative substitution" is intended to mean the substitution of an amino acid with another that has similar chemical properties (size, charge or polarity), which generally does not modify the functional properties of the protein.

A protein that has an amino acid sequence having at least X % similarity with a reference sequence is defined, in the present invention, as a protein whose sequence can include up to 100-X non-conservative alterations per 100 amino acids of the reference sequence. For the purpose of the present invention, the term "non-conservative alterations" includes deletions, non-conservative substitutions, or consecutive or dispersed insertions of amino acids in the reference sequence.

Included in the proteins as defined in (g), are the proteins that are variants of the sequence SEQ ID NO. 2, i.e. the variant proteins encoded by the variant polynucleotides as defined above, in particular the proteins whose amino acid sequence has at least one mutation corresponding in particular to a truncation, a deletion, a substitution and/or an addition of at least one amino acid residue relative to the sequence SEQ ID NO. 2.

Preferably, the variant proteins have a mutation associated with diabetes or with hyperinsulinism.

According to an advantageous embodiment of the use according to the present invention, said isolated polynucleotide as defined in (c) is a polynucleotide that is a variant of the sequence SEQ ID NO. 1, comprising a mutation which results in a modification of the amino acid sequence of the protein encoded by the sequence SEQ ID NO. 1.

According to another advantageous embodiment of the use according to the present invention, said isolated polynucleotides as defined in (b) or in (d) are chosen from the pair of primers SEQ ID NO. 3 and SEQ ID NO. 4 and the pair of primers SEQ ID NO. 5 and SEQ ID NO. 6.

According to yet another advantageous embodiment of the use according to the present invention, said isolated polynucleotide can be obtained by amplification using the pair of primers as defined above.

According to yet another advantageous embodiment of the use according to the present invention, said polynucleotide as defined in (d) is a small interfering RNA (siRNA) which, by interaction with the mRNAs corresponding to said polynucleotide, will bring about their degradation.

According to yet another advantageous embodiment of the use according to the present invention, said protein as defined in (g) is a variant of the sequence SEQ ID NO. 2, that has a mutation associated with diabetes or with hyperinsulinism.

According to yet another advantageous embodiment of the use according to the present invention, said fragment as defined in (f) has a sequence chosen from the sequences SEQ ID NO. 7, SEQ ID NO. 8, SEQ ID NO. 9 and SEQ ID NO. 10.

A subject of the present invention is also a polynucleotide as defined above, with the exception:
- of the fragments of at least 15 consecutive nucleotides included in the sequences having the accession numbers, in the NCBI database, No. AX526723, No. AX526725 and No. AX526727,
- of the ESTs having the accession numbers, in the GenBank database, BM565129, BM310003, BM875526, BG655918, BQ417284, BQ267316, BU072134, BQ267526, BQ270198, BU581447, BU070173, BQ631692 and BU949895, and also of the sequences having the accession numbers, in the NCBI database, AX526723, AX526725 and AX526727.

The fragments according to the invention can in particular be used as probes or as primers for detecting/amplifying polynucleotides (RNA or genomic DNA) corresponding to the polynucleotide according to the invention in other organisms.

Preferably, the pairs of primers that can be used according to the invention are those corresponding to the pairs defined by the sequences SEQ ID NO. 3 and SEQ ID NO. 4 and by the sequences SEQ ID NO. 5 and SEQ ID NO. 6.

A subject of the invention is also the polynucleotides that can be obtained by amplification using the primers as defined above.

According to an advantageous embodiment of the polynucleotide according to the invention, it is a small interfering RNA corresponding to the polynucleotide as defined above, less than 30 nucleotides in length, preferably between 20 and 23 nucleotides in length, which, by interaction with the mRNAs corresponding to said polynucleotide, will bring about their degradation. These siRNAs can be obtained by any method known to those skilled in the art, for example by chemical synthesis or else by expression from a vector.

The invention encompasses the sense oligonucleotides corresponding to the polynucleotides of the invention which, by interaction with proteins involved in the regulation of the expression of said polynucleotide of the invention, will induce either inhibition or activation of this expression.

The probes and primers according to the invention can be directly or indirectly labeled with a radioactive or non-radioactive compound by methods well known to those skilled in the art, in order to obtain a detectable and/or quantifiable signal.

The labeling of the primers or of the probes according to the invention is carried out with radioactive elements or with non-radioactive molecules. Among the radioactive isotopes used, mention may be made of $^{32}P$, $^{33}P$, $^{35}S$, $^{3}H$ or $^{125}I$. The non-radioactive entities are selected from ligands such as biotin, avidin, streptavidin or digoxigenin, haptens, dyes, and luminescent agents such as radioluminescent, chemiluminescent, bioluminescent, fluorescent or phosphorescent agents.

The polynucleotides according to the invention can thus be used as primers and/or probes in methods using in particular the PCR (polymerase chain reaction) technique (U.S. Pat. No. 4,683,202). Other techniques for amplifying the target nucleic acid can be advantageously used as an alternative to PCR. A large number of methods currently exist for this amplification, for instance the SDA (strand displacement amplification) technique, the TAS (transcription-based amplification system) technique, the 3SR (self-sustained sequence replication) technique, the NASBA (nucleic acid sequence based amplification) technique, the TMA (transcription mediated amplification) technique, the LCR (ligase chain reaction) technique, the RCR (repair chain reaction) technique, the CPR (cycling probe reaction) technique, and the Q-beta-replicase amplification technique. PCR-SSCP, which makes it possible to detect point mutations, may also be mentioned.

These techniques are of course entirely known to those skilled in the art.

As probes or as primers, the various polynucleotides of the invention make it possible either to determine the transcription profile of the corresponding gene or any possible alteration of this profile in a biological sample, or to demonstrate the corresponding gene, allelic variants of this gene or any possible functional alteration of this gene (substantial change in the activity of the protein encoded by said gene) resulting from a mutation (insertion, deletion or substitution) of one or more nucleotides in at least one exon of said gene. Such mutations include in particular deletions, insertions or non-conservative substitutions in codons corresponding to amino acid residues located in a domain that is essential for the biological activity of the protein.

Thus, a subject of the invention is a method for determining the transcription profile of the gene corresponding to the polynucleotide of the invention, or an alteration of said profile, in a biological sample, comprising a first step consisting in obtaining the total RNA from the biological sample, a second step consisting in bringing said RNA into contact with a labeled probe consisting of a polynucleotide according to the invention, under conditions appropriate for hybridization between the RNAs and the probe, and a third step consisting in revealing, by any appropriate means, the hybrids formed.

According to one embodiment of said method, the second step can be a step consisting of reverse transcription and/or of amplification of the transcripts, carried out using a pair of primers as described above, and the third step can be a step consisting in revealing, by any appropriate means, the amplified nucleic acids formed.

Said method for determining the transcription profile of the gene can also comprise a step consisting in evaluating the level of transcription of the gene by comparison with a control sample selected beforehand and, optionally, studying its correlation with a detectable phenotype, for instance the amount of proinsulin converted to mature insulin, the insulin content of the cells, the amount of insulin secreted in response to a stimulation with glucose, the intracellular or intravesicular zinc concentration, or else the amount of protein (gene product) expressed at the surface of the cell. Said control sample may, for example, consist of a biological sample exhibiting normal or altered transcription of the gene corresponding to the polynucleotide of the invention to which said method for determining the transcription profile of the gene is applied under the same conditions.

A subject of the invention is also a method for demonstrating the gene corresponding to the polynucleotide of the invention or the allelic variants of said gene or a functional alteration of this gene, in a biological sample, comprising a first step consisting in obtaining, by any appropriate means, the DNA from the biological sample, a second step consisting in bringing said DNA into contact with a labeled probe consisting of a polynucleotide according to the invention, under conditions appropriate for specific hybridization between the DNAs and the probe, and a third step consisting in revealing, by any appropriate means, the hybrids formed.

According to an advantageous embodiment of said method, the second step can be an amplification step carried out using a pair of primers as described above, and the third step can be a step consisting in revealing, by any appropriate means, the amplified nucleic acids formed. The method can optionally comprise a fourth step consisting in isolating and sequencing the nucleic acids demonstrated.

The latter method can also make it possible to isolate an allele of the gene corresponding to the polynucleotide of the invention, associated with a detectable phenotype, for instance a variation in post-prandial blood glucose, the presence or absence of insulin secretion, the level of circulating glucose or the amount of insulin secreted in response to a stimulation with glucose and, in general, with a pathology of the type I or II diabetes kind, or else with a zinc metabolism anomaly. The zinc excreted during the release of insulin acts on potassium channels that are responsible, via calcium channels, for this exocytosis. There is therefore a feedback loop [14]. The polypeptide of the invention is involved in zinc accumulation in the vesicles containing insulin, and is also found, during the exocytosis, on the plasma membrane. Mutants of the proteins could therefore modify either the amount of zinc present in the vesicles or the pericellular concentration of zinc, and therefore modify the state of opening of the potassium channel, resulting, depending on the effect of the mutation, in a decrease or an increase in insulin excretion (type I diabetes or hyperinsulinism). In this particular method, the biological sample will be a sample originating from an individual expressing said detectable phenotype.

These methods, particularly those based on the search for mutations in the gene, may allow the preventive demonstration of a predisposition to diabetes, or the diagnosis of diabetes or of any disease associated with diabetes, or the adaptation, in terms of molecule or of dosage, of antidiabetic treatments.

A subject of the invention is also a kit of reagents for carrying out the methods described above, comprising:

a) at least one probe or one pair of primers according to the invention;

b) the reagents required for carrying out a hybridization reaction between said probe and/or said primers and the nucleic acid of the biological sample to be tested;

c) the reagents required for carrying out an amplification reaction;

d) the reagents required for detecting and/or assaying the hybrid formed between said probe and the nucleic acid of the biological sample, or the amplified nucleic acids formed.

Such a kit can also contain positive or negative controls in order to ensure the quality of the results obtained. They may also contain the reagents required for preparing the nucleic acids from the biological sample.

Another subject of the invention is a DNA chip comprising at least one polynucleotide according to the invention.

Yet another subject of the invention is the use of a polynucleotide as defined above, for preparing a DNA chip. Those skilled in the art are capable, according to the support selected, of choosing the appropriate preparation technique for producing such a chip, for instance by deposition of oligonucleotides onto a glass or nylon support, or by chemical or electrochemical grafting of oligonucleotides.

The polynucleotide of the invention can be used, in vitro, as a means for studying:

a) the overexpression of the transporter (ZnT-8) in model cell lines (INS-1 rat insulinoma for example) and the impact on insulin secretion in response to a stimulation with glucose;

b) the sensitivity of the cells to cell death (apoptosis) induced by conditions of oxidative stress or of low or high zinc concentration;

c) the steps of differentiation of stem cells into insulin-secreting cells in response to various exogenous stimulations (growth factors, pancreatic extracts).

The invention also relates to the protein encoded by the polynucleotide according to the invention.

For the purpose of the present invention, the term "protein" is intended to denote a precise series of modified or non-modified amino acids possibly comprising non-natural amino acids.

The protein according to the invention is obtained either from a beta cell, or by chemical synthesis, or by recombinant DNA techniques, in particular using an expression vector comprising an insert consisting of the polynucleotide as defined above.

The invention also relates to the use of a polynucleotide as defined above, for producing a ZnT-8 protein as defined above.

The protein according to the present invention, when it is obtained by chemical synthesis, can be obtained by one of the many known peptide synthesis pathways, for example techniques using solid phases or techniques using partial solid phases, by fragment condensation or by conventional synthesis in solution. In this case, the sequence of the protein can be modified in order to improve its solubility, in particular in aqueous solvents. Such modifications are known to those skilled in the art, for example the deletion of hydrophobic domains or the substitution of hydrophobic amino acids with hydrophilic amino acids.

Preferably, a protein according to the invention is a protein comprising or having the sequence SEQ ID NO. 2 (corresponding to the protein encoded by the ZnT-8 gene).

A subject of the invention is also a fragment of the protein as defined above, characterized in that it is selected from the group consisting of the sequences SEQ ID NO. 7, SEQ ID NO. 8, SEQ ID NO. 9 and SEQ ID NO. 10.

Another subject of the invention is a protein chip comprising a protein or a protein fragment as defined above.

Yet another subject of the invention is the use of a protein or of a protein fragment as defined above, for preparing a protein chip. As for the DNA chips, those skilled in the art are capable, according to the support chosen, of choosing the appropriate preparation technique for producing such a chip.

The protein, the protein fragment or the protein chip as defined above can be used for detecting the presence of antibodies directed against said proteins in the serum of an individual.

The invention also relates to the use of the protein or of the protein fragment as defined above, for measurements by means of immunochemical and immuno-enzymatic methods, and also the search for autoantibodies directed against the protein according to the invention.

A subject of the invention is also a cloning and/or expression vector into which the polynucleotide of the invention is inserted.

Such a vector can contain the elements required for the expression and, optionally, the secretion of the protein in a host cell.

Said vectors preferably comprise: a promoter, translation initiation and termination signals, and also appropriate regulatory regions for transcription. It should be possible for them to be maintained stably in the cell and they may optionally comprise sequences encoding particular signals specifying the secretion of the translated protein, for example a strong ubiquitous promoter, or a promoter that is selective for a particular cell and/or tissue type, for instance the pancreas. These various control sequences are chosen according to the cellular host used.

The polynucleotide according to the invention can be inserted into vectors that replicate autonomously in the chosen host or vectors that integrate in the chosen host.

Among the autonomously replicating systems, systems of plasmid or viral type are preferably used, according to the host cell. The viral vectors may in particular be adenoviruses, retroviruses, lentiviruses, poxviruses or herpesviruses. Those skilled in the art are aware of the technology that can be used for each of these systems.

When integration of the sequence into the chromosomes of the host cell is desired, it is possible to use, for example, systems of the plasmid or viral type; such viruses are, for example, retroviruses or adeno-associated viruses (AAVs).

Among the non-viral vectors, preference is given to naked polynucleotides such as naked DNA or RNA, bacterial artificial chromosomes (BACs), yeast artificial chromosomes (YACs) for expression in yeast, mouse artificial chromosomes (MACs) for expression in murine cells and, preferably, human artificial chromosomes (HACs) for expression in human cells.

Such vectors are prepared according to the methods commonly used by those skilled in the art, and the recombinant vectors resulting therefrom can be introduced into the appropriate host by standard methods, for instance lipofection, electroporation, thermal shock, transformation after chemical membrane permeabilization, cell fusion.

A subject of the invention is also the modified host cells, in particular the eukaryotic and prokaryotic cells, into which at least one polynucleotide according to the invention or at least one vector according to the invention has been introduced.

Among the cells that can be used for the purposes of the present invention, mention may be made of bacterial cells, yeast cells, animal cells, in particular mammalian cells, or else plant cells. Mention may also be made of insect cells in which methods implementing, for example, baculoviruses can be used.

A subject of the invention is also the non-human transgenic organisms, such as the transgenic animals or plants, in which all or some of the cells contain the polynucleotide according to the invention or the vector of the invention, in a free or integrated form.

Preferably according to the invention, the non-human transgenic organisms are those carrying cells containing a polynucleotide according to the invention that is non-functional or that carries a mutation.

According to the invention, the transgenic animals are preferably mammals, more preferably rodents, in particular mice, rats or rabbits, and the Suidae, in particular pigs.

The transgenic animals can be obtained by any conventional method known to those skilled in the art, for instance by homologous recombination in embryonic stem cells, transfer of these stem cells to embryos, selection of the chimeras affected in the reproductive lines, and growth of said chimeras.

The cells or the transgenic animals or plants according to the invention can thus express or overexpress the gene encoding the protein according to the invention or their homologous gene, or express said gene into which a mutation has been introduced.

The transgenic animals can be used, for example, as models for studying the etiology of diabetes.

The transgenic organisms according to the invention can be used for producing the protein according to the invention.

The protein according to the invention can be purified according to the techniques known to those skilled in the art. Thus, the protein can be purified from cell lysates and extracts, or from the culture medium supernatant, by methods used individually or in combination, such as fractionation, chromatography methods, immunoaffinity techniques using specific monoclonal or polyclonal antibodies, etc. Preferably, the protein according to the invention is purified according to a method comprising a first step consisting of separation of the membrane proteins by centrifugation, followed by a second step consisting of purification by immunoaffinity according to the method described by T. C. Thomas, M. G. McNamee, (Purification of membrane proteins. Section IX, pp 499-520, in Methods in Enzymology, Guide to Protein Purification, edited by M. P. Deutscher, vol. 182, Academic Press, New York, 1990).

A subject of the invention is also a method for preparing the recombinant ZnT-8 protein, characterized in that it comprises culturing the modified cells of the present invention, in particular mammalian cells, or the cells derived from the non-human transgenic organisms according to the invention, under conditions that allow the expression of said protein, and purifying said recombinant protein.

A subject of the invention is also a protein, characterized in that it can be obtained by means of any one of the preparation methods described above.

The protein obtained as indicated above can be in both glycosylated and non-glycosylated form, and may or may not have the tertiary structure of the natural protein.

The inventors have also been able to show, by means of a study of the transmembrane potential, that the secondary structure of the protein of the invention has 3 extracellular amino acid loops (amino acids 96-106, 164-176, and 241-245) against which monoclonal or polyclonal antibodies can be produced.

A subject of the invention is thus also monoclonal or polyclonal antibodies, characterized in that they are capable of specifically recognizing a protein according to the invention.

Preferably, the antibodies specifically recognize the protein of sequence SEQ ID NO. 2, its fragments, or the variants of said protein as defined above.

Preferably, the antibodies according to the invention specifically recognize the extracellular loops of the protein according to the invention, corresponding to SEQ ID NO. 7, SEQ ID NO. 8 and SEQ ID NO. 10 (PEP1, PEP2 and PEP4), and/or an intracellular loop of the protein according to the invention, corresponding to SEQ ID NO. 9 (PEP3).

The antibodies according to the invention are, for example, chimeric antibodies, humanized antibodies, or Fab or F(ab')2 fragments. They can also be in the form of immunoconjugates or of labeled antibodies in order to obtain a detectable and/or quantifiable signal.

Said antibodies can be obtained directly from human serum, or from serum of animals immunized with the proteins according to the invention, in particular those produced by genetic recombination or by peptide synthesis.

The specific polyclonal antibodies can be obtained according to the usual procedures. The specific monoclonal antibodies can be obtained according to the conventional hybridoma culture method.

Another subject of the invention is a protein chip comprising at least one antibody according to the invention.

The invention also relates to the use of an antibody according to the invention, for preparing a protein chip comprising said antibody. Those skilled in the art are capable, according to the support chosen, of choosing the appropriate preparation technique for producing such a chip.

A subject of the invention is also the use of the antibodies or of an antibody chip according to the invention, for detecting and/or purifying a protein according to the invention, preferably the extracellular or intracellular loops of said protein, preferably the sequences corresponding to SEQ ID NO. 7 to SEQ ID NO. 10.

In general, the antibodies of the invention can be advantageously used in any situation where the expression of a normal or mutated protein according to the invention must be observed.

In particular, the monoclonal antibodies can be used for detecting these proteins in a biological sample. They thus constitute a means of immunocytochemical or immunohistochemical analysis of the expression of the proteins according to the invention, in particular the protein of SEQ ID NO. 2 or one of its variants, on specific tissue sections. In general, for such analyses, the antibodies used are labeled in order to be detectable, for example with immunofluorescent compounds, by means of gold labeling, or in the form of enzymatic immunoconjugates.

They can in particular make it possible to demonstrate abnormal expression of these proteins in the biological tissues or samples.

A subject of the invention is also a method for detecting the ZnT-8 protein in a biological sample, comprising a first step consisting in bringing the biological sample into contact with an antibody according to the invention, and a second step consisting in demonstrating, by any appropriate means, the antigen-antibody complex formed.

A subject of the invention is also a kit for carrying out the method described above, comprising:

a) at least one monoclonal or polyclonal antibody according to the invention;

b) the reagents for detecting the antigen-antibody complex produced during the immunoreaction.

According to a particular embodiment of the invention, the kit can optionally comprise reagents for constituting a medium that allows the immunoreaction.

The antibodies according to the invention can also be used for detecting and/or sorting islets of Langerhans, preferably beta cells, using human or animal pancreas, in particular mouse, rat, rabbit and porcine pancreas. This sorting can be carried out using a flow cytometry (FACS) device as regards the isolated cells. For the islets, labeling thereof could improve the current separation methods: separation by density gradient with Ficoll, euro-Ficoll or Ficoll-sodium diatrizoate, or the method of choice, which is an albumin gradient on a cell separator.

Thus, a subject of the invention is a method for selecting the beta cells of islets of Langerhans, comprising a first step consisting in bringing the cells of a biological sample liable to contain such islets and/or cells into contact with an antibody according to the invention, a second step consisting in demonstrating, by any appropriate means, the cells labeled with the antibody, and a third step consisting in isolating, by any appropriate means, the labeled cells.

The antibodies according to the invention can also be used for following the process of differentiation of stem cells into beta cells of islets of Langerhans, that are particularly human or animal cells, and also sorting these cells expressing the ZnT-8 protein, particularly the protein of sequence SEQ ID NO. 2, after differentiation.

Thus, a subject of the invention is a method for following the process of differentiation of stem cells into pancreatic islet cells or into beta cells, comprising a step consisting in bringing the cells of a biological sample liable to contain said stem cells undergoing differentiation into contact with an antibody according to the invention, a second step consisting in demonstrating, by any appropriate means, the cells labeled with the antibody, and a third step consisting in visualizing, by any appropriate means, the labeled cells.

Said method may also comprise an additional step consisting in isolating, by any appropriate means, the labeled cells.

The polynucleotide, the cell, the transgenic organism or the DNA chip according to the invention can be used for screening for chemical or biochemical compounds that can directly or indirectly interact, in vitro or in vivo, with the polynucleotide according to the invention and/or modulate the expression of said polynucleotide.

Thus, a subject of the invention is a method of screening for a chemical or biochemical compound that can directly or indirectly interact, in vitro or in vivo, with the polynucleotide according to the invention, characterized in that it comprises a first step consisting in a candidate chemical or biochemical compound into contact with the polynucleotide, the cell, the non-human transgenic organism or the DNA chip according to the invention and a second step consisting in detecting the complex formed between the candidate chemical or biochemical compound and the polynucleotide, the cell, the non-human transgenic organism or the DNA chip according to the invention.

A subject of the invention is also a method of screening for a chemical or biochemical compound that can directly or indirectly modulate, in vitro or in vivo, the expression of the polynucleotide according to the invention, characterized in that it comprises a first step consisting in bringing a candidate chemical or biochemical compound into contact with the polynucleotide, the cell, the non-human transgenic organism or the DNA chip according to the invention, and a second step consisting in measuring, by any appropriate means, the expression of said polynucleotide.

The protein, the cell, the transgenic organism or the protein chip according to the invention can be used for screening for chemical or biochemical compounds that can directly or indirectly interact, in vitro or in vivo, with the protein according to the invention, and/or that can modulate the expression or the activity of said protein.

Thus, a subject of the invention is a method of screening for a chemical or biochemical compound that can directly or indirectly interact, in vitro or in vivo, with the protein according to the invention, characterized in that it comprises a first step consisting in bringing a candidate chemical or biochemical compound into contact with the protein, the cell, the non-human transgenic organism or the protein chip according to the invention, and a second step consisting in detecting the complex formed between the candidate chemical or biochemical compound and the protein, the cell, the non-human transgenic organism or the protein chip according to the invention.

A subject of the invention is also a method of screening for a chemical or biochemical compound that can directly or indirectly modulate, in vitro or in vivo, the expression and/or the activity of the protein according to the invention, characterized in that it comprises a first step consisting in bringing a candidate chemical or biochemical compound into contact with the protein, the cell, the non-human transgenic organism or the protein chip according to the invention, and a second step consisting in measuring, by any appropriate means, the expression and/or the activity of said protein.

A subject of the invention is also the polynucleotide, the protein, the antibodies, the vectors or the transformed cells, according to the invention, as medicinal products.

The polynucleotide, the protein, the antibodies, the vectors or the transformed cells, according to the invention, can be used in the preparation of a medicinal product intended for the prevention and/or the treatment of diabetes, particularly that associated with the presence of at least one mutation of the gene corresponding to SEQ ID NO. 1, and/or with abnormal expression of the protein corresponding to SEQ ID NO. 2, or intended for the prevention and/or the treatment of hyperinsulinism when abnormal expression, maturation or secretion with respect to the insulin gene is observed, or intended to regulate the maturation and the secretion of insulin in the beta cells and/or in cells that are to be modified for the purpose of insulin secretion, or intended to regulate beta cell apoptosis phenomena.

Abnormal expression means overexpression, underexpression, or the expression of a mutated protein. Abnormal maturation means no proteolysis or insufficient proteolysis of proinsulin to insulin, or no cocrystallization, insufficient cocrystallization or too much cocrystallization of insulin and zinc in the intracellular secretory vesicles.

A subject of the invention is also the use of a polynucleotide, of a protein or of an antibody according to the invention, for determining an allelic variability, a mutation, a deletion, a loss of heterozygocity or any genetic anomaly of the gene encoding the protein according to the invention. It is possible to detect the mutations in the sequence of the ZnT-8 gene directly by analysis of the nucleic acid and of the sequences according to the invention (genomic DNA, RNA, or cDNA), but also by means of the protein according to the invention. In particular, the use of an antibody according to the invention that recognizes an epitope carrying a mutation makes it possible to differentiate a "normal" protein from a protein "associated with a pathology".

Those skilled in the art also know how to carry out techniques of studying the alteration in expression of a gene, for example by analysis of the mRNA, in particular by Northern blotting or by RT-PCR with probes or primers according to the invention, or else by analysis of the expressed protein, in particular by Western blotting, using antibodies according to the invention.

Besides the above provisions, the invention also comprises other provisions that will emerge from the following description, which refers to examples of implementation of the invention and also to the attached drawings, in which:

FIG. 1 illustrates the RT-PCR analysis of the tissue expression of the messenger RNA encoding the ZnT-8 protein (A), by comparison with the expression of the ubiquitous actin messenger (B). 1: brain, 2: heart, 3: kidney, 4: spleen, 5: liver, 6: colon, 7: lung, 8: small intestine, 9: muscle, 10: stomach, 11: testes, 12: placenta, 13: salivary glands, 14: thyroid, 15: adrenal glands, 16: pancreas, 17: ovaries, 18: uterus, 19: prostate, 20: skin, 21: leukocytes, 22: bone marrow, 23: fetal brain, 24: fetal liver. The expression of said mRNA is detected only in the pancreas (lane 16).

FIG. 2 illustrates the RT-PCR analysis of the expression of the messenger RNA encoding the ZnT-8 protein, in: a rat insulinoma line (INS-1, lane 1), fetal (lane 2) and adult (lane 3) human pancreatic islets, by comparison with an epithelial cell line (Hela line). The mRNA is detected in the rat insulinoma line and the adult and fetal pancreatic islets, whereas no transcript is detected in the epithelial cells (Hela line). The actin messenger is used as control.

Figure 1:
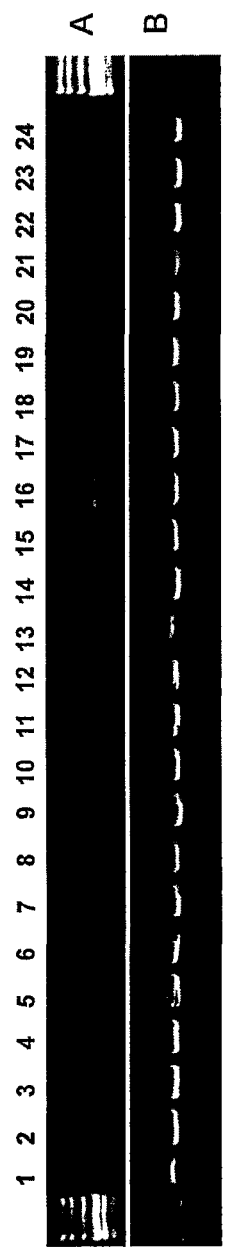

The following examples are illustrations of the invention and in no way limit it.

EXAMPLE 1

Cloning of the cDNA Encoding the ZnT-8 Protein

The gene encoding the ZnT-8 protein, called ZnT-8 gene, was identified by bioinformatics, by searching for genes homologous to those of the ZnT family, using the available human genome sequences. Analysis of the genomic sequences made it possible to localize and define the intron/exon organization of the ZnT-8 gene.

The cDNA encoding ZnT-8 was amplified by RT-PCR from mRNA of human pancreatic islets prepared according to the technique given in T. Kenmochi et al. (*Pancreas*, 2000, 20, 2, 184-90), using the pair of primers (SEQ ID NO. 5: 5'-ACTCTAGAATGGAGTTTCTTGAAAGAACGT A and SEQ ID NO. 6: 5'-AATCTA GAGTCACAGGGGTCT-TCACAGA), defined from the sequence of the ZnT-8 gene.

More precisely, the total RNA was extracted from the islets, using the RNA extraction kit (Roche) according to the producer's instructions. The RNA thus obtained was assayed by measuring the absorbance at 250 nm, and conserved at −80° C.

The amplification was carried out using the Titan one tube RT-PCR kit (Roche) according to the producer's instructions, and the pair of primers SEQ ID NO. 5 and SEQ ID NO. 6. The reverse transcription was carried out at 52° C. for 30 min and the cDNAs synthesized were then amplified by means of 30 cycles (30 s at 94° C., 30 s at 53° C., 1 min at 72° C.) and a final elongation of 5 min at 72° C. The amplification products were separated by agarose gel electrophoresis (1.5%) in the presence of ethidium bromide, and the 1123 base pair amplification product comprising the cDNA sequence having the sequence SEQ ID NO. 1 was purified using the nucleic acid purification kit (QIAGEN), according to the producer's instructions.

EXAMPLE 2

Analysis of the Tissue Expression of the Messenger RNA Encoding the ZnT-8 Protein The expression of the messenger RNA encoding the ZnT-8 protein was analyzed by PCR on commercial cDNAs prepared from various human tissues, using the following primers: SEQ ID NO. 3: 5'-GAT GCT GCC CAC CTC TTA ATT GAC and SEQ ID NO. 4: 5'-TCA TCT TTT CCA TCC TGG TCT TGG. The primers (SEQ ID NO. 3 and SEQ ID NO. 4) were chosen in 2 different exons in order to avoid amplification of a genomic sequence. The tissues tested are: 1: brain, 2: heart, 3: kidney, 4: spleen, 5: liver, 6: colon, 7: lung, 8: small intestine, 9: muscle, 10: stomach, 11: testes, 12: placenta, 13: salivary gland, 14: thyroid, 15: cortico adrenal gland, 16: pancreas, 17: ovary, 18: uterus, 19: prostate, 20: skin, 21: blood leukocytes, 22: bone marrow, 23: fetal brain, 24: fetal liver.

More precisely, 2 μl of cDNA were mixed with the 2 specific primers (1 μM final concentration) and a conventional PCR mixture (1 unit of Taq DNA polymerase, buffer with 1.5 mM magnesium, 10 mM dNTP). The amplification was carried out by means of 30 cycles (30 s at 94° C., 30 s at 53° C., 1 min at 72° C.) and a final elongation step of 5 min at 72° C. The products were then analyzed by agarose gel electrophoresis (1.5%) in the presence of ethidium bromide.

The results given in FIG. 1 show that, by comparison with the actin messenger used as a control (FIG. 1B), the mRNA corresponding to the polynucleotide of the invention is expressed only in the pancreatic cells (lane 16 of FIG. 1A), and not in the cells of the other 23 tissues analyzed (lanes 1 to 15 and 17 to 24 of FIG. 1A).

EXAMPLE 3

Expression of the Messenger RNA Corresponding to the Polynucleotide of the Invention in Fetal and Adult Pancreas Cells and in a Rat Insulinoma Line (INS-1)

The analysis of the expression of the messenger RNA encoding the ZnT-8 protein was carried out by RT-PCR, using RNA from various human tissues: adult and fetal human pancreatic islets, rat insulinoma line (INS-1; Asfari M. et al., *Endocrinology*, 1992, 130, 1, 167-78), by comparison with a human epithelial cell line (Hela) used as a control. $10^6$ cells are washed twice with phosphate buffer (PBS) and then centrifuged for 3 min at 2000 g. The total RNA is extracted as described in example 1, and the RNA concentration is adjusted to 1 ng/μl for ZnT-8 or 1 pg/μl for the β-actin control. The transcripts are amplified and the amplification products are then analyzed, as described in example 2.

Figure 2:
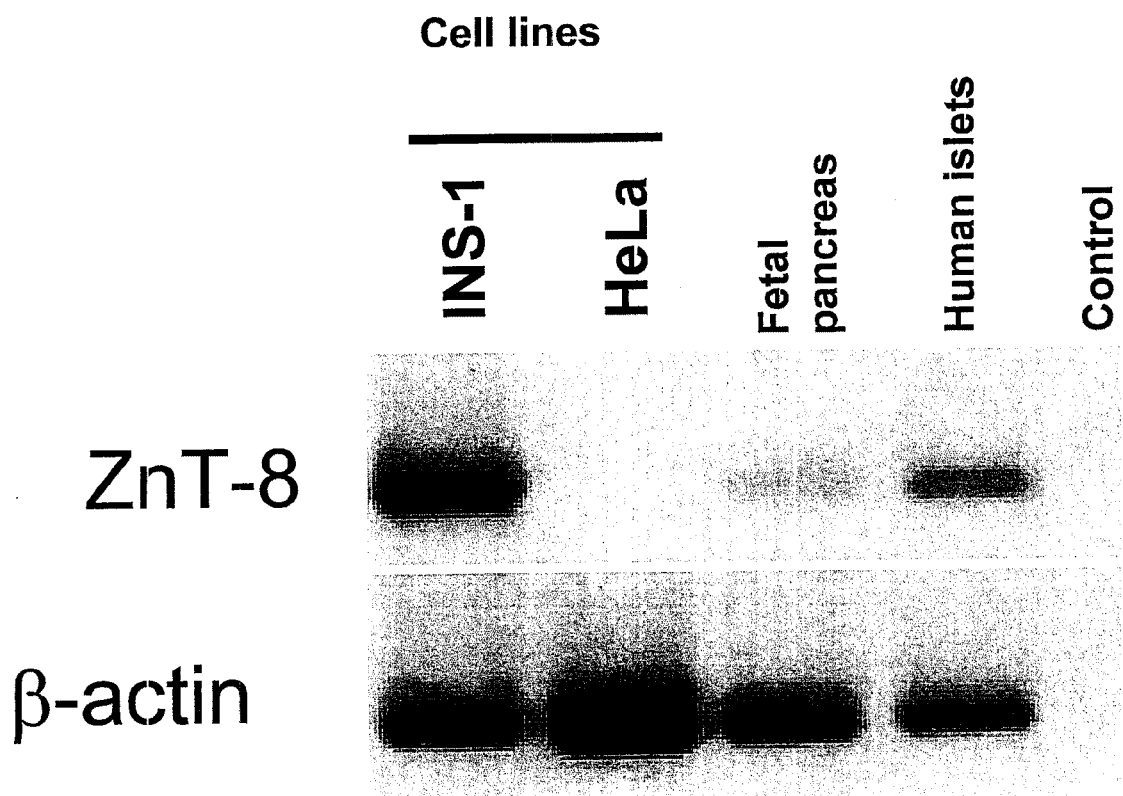

The results given in FIG. 2 show that the mRNA encoding the ZnT-8 protein is expressed in the cells of the fetal and adult human pancreatic islets and in a rat insulinoma line (INS-1), but not in an epithelial cell line (Hela line).

EXAMPLE 4

Expression of a ZnT-8/GFP Fusion Protein

The protein is the human protein encoded by the cDNA corresponding to the sequence SEQ ID NO. 1 (ZnT-8). The 1123 base pair PCR product obtained according to example 1 was digested with the XbaI restriction enzyme and then cloned into the vector pcDNA3.1-CT-GFP (Invitrogen), to give the vector called pZnT-8-GFP, which was verified by sequencing.

The vector pZnT-8-GFP was transiently transfected into an epithelial cell line (Hela) and stably transfected into a rat insulinoma line (INS-1).

The Hela epithelial cells (ATCC number CCL-2) are cultured in Opti-MEM medium (Modified Eagle's Medium, Life Technologies) supplemented with 5% of decomplemented calf serum and 2 mM of glutamine. The cells are incubated at 37° C. in a humidified atmosphere enriched with 5% of $CO_2$.

The INS-1 cells are cultured in RPMI medium (Life Technologies) supplemented with: fetal calf serum (10%), 2-mercaptoethan-1-ol (50 μM), sodium pyruvate (1 mM), HEPES (10 mM), L-glutamine (2 mM), 100 U/ml penicillin and streptomycin (100 μg/ml).

The cells, cultured in 35 mm Petri dishes, are transfected with the vector pZnT-8-GFP (1 μg of DNA per $10^6$ cells) using the Exgen500 (Euromedex) reagent according to the producer's instructions. After transfection with the vector ZnT-8-GFP, the INS-1 cells are selected, and cloned in the same medium as previously, supplemented with 400 μg/ml of G418, and then the fluorescence of the clones is observed under an inverted fluorescence microscope (Axiovert, Zeiss) using the following parameters: excitation wavelength: 450-490 nm; emission wavelength: 520 nm.

Expression of the ZnT-8-GFP fusion protein in the Hela cells is analyzed 48 hours after transfection, by observation of the fluorescence as specified above, for the stably transfected INS-1 cell clones.

Figure 3:
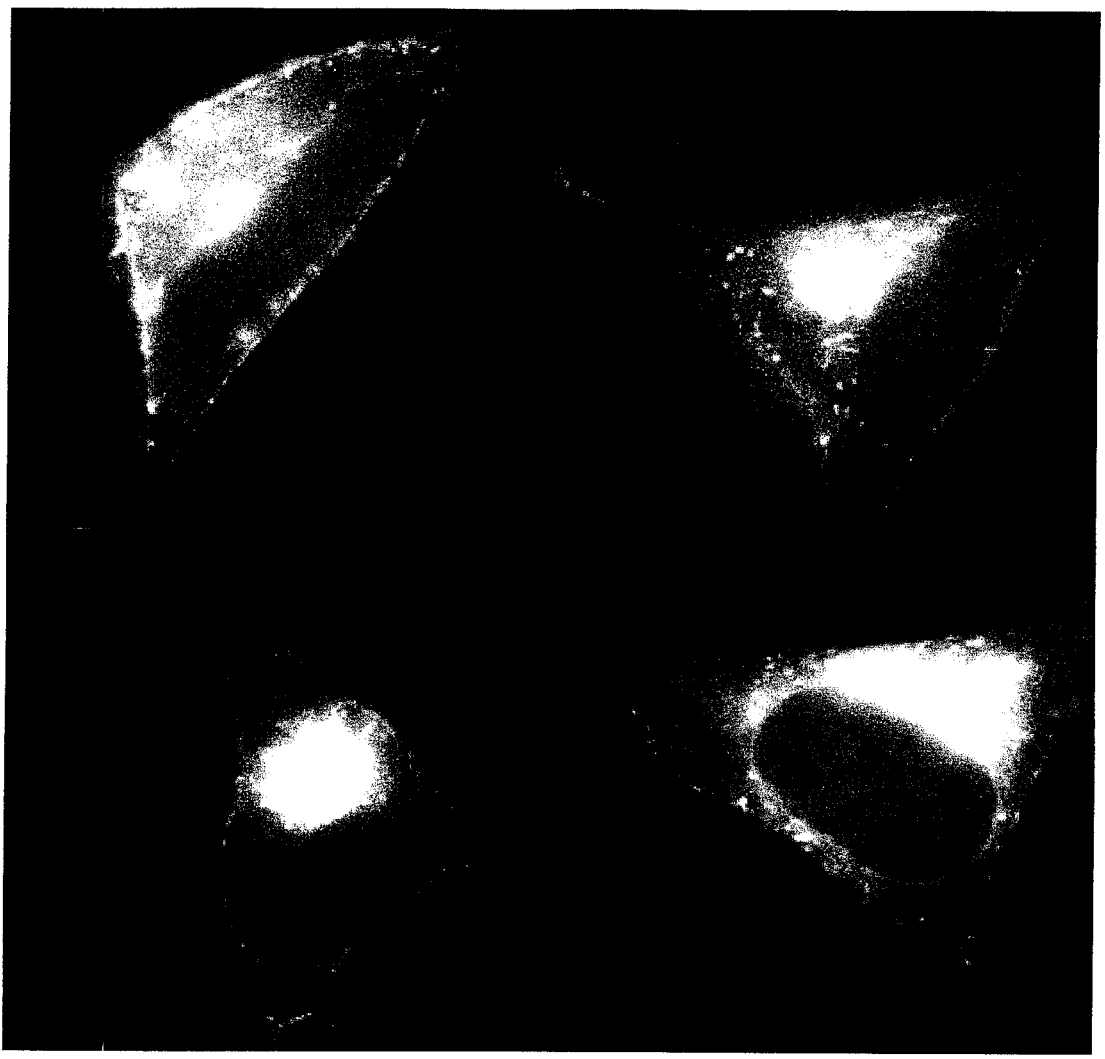
FIG. 3 illustrates the fluorescence microscopy analysis of the localization of the ZnT-8-GFP fusion protein in transfected epithelial cells (Hela line). The fluorescence is localized in the intracytoplasmic vesicles and also at the plasma membrane.

The results given in FIG. 3 (Hela line) show that the ZnT-8 protein is localized in intracytoplasmic vesicles and also on the plasma membrane; this localization demonstrates that the ZnT-8 protein takes the extracellular excretion pathway and is at the surface of the cell.

Figure 4:
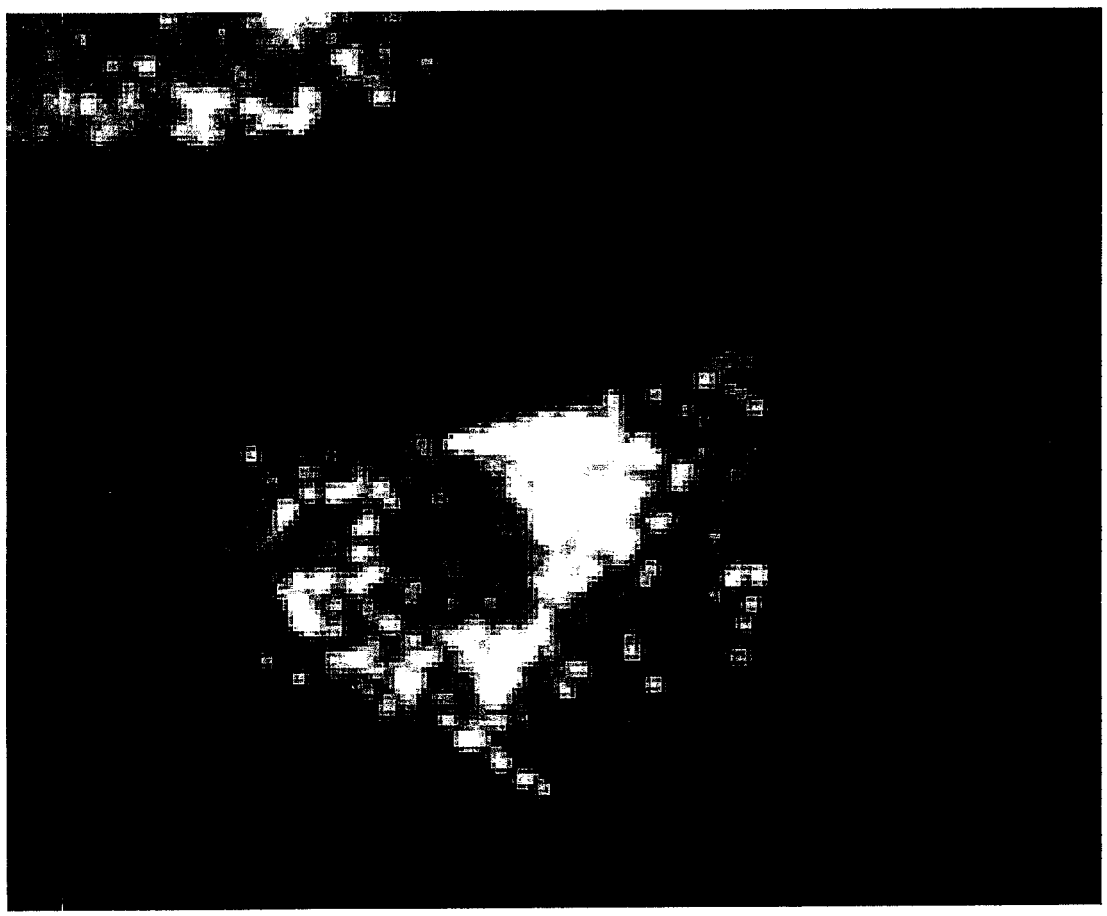
FIG. 4 illustrates the fluorescence microscopy analysis of the localization of the ZnT-8-GFP fusion protein in transfected rat insulinoma cells (INS-1 line). The fluorescence is localized in the secretory vesicles, indicating a role for ZnT-8 in the maturation and exocytosis of insulin.

The results given in FIG. 4 (INS-1 line) show that the ZnT-8 protein is localized in the insulin secretory vesicles; this localization indicates that ZnT-8 is involved in the maturation of insulin; in addition, since this experiment is carried out at the basal level (in the absence of stimulation with glucose), the protein will also be present on the plasma membrane during insulin exocytosis, after stimulation with glucose.

EXAMPLE 5

Analysis of the Sequence of the ZnT-8 Protein

The analysis of the primary sequence of ZnT-8 and the prediction of the transmembrane domains were carried out with the TMpred)(hypertext transfer protocol on the worldwide web at ch.embnet.org/software/TMPRED_form.html) and SOSUI (hypertext transfer protocol on the worldwide web at sosui.proteome.bio.tuat.ac.jp.sosuimenu).html programs.

The complete ZnT-8 protein has 6 predicted transmembrane domains (amino acids 74-95, 107-126, 141-163, 177-196, 216-240, and 246-267), the N- and C-terminal ends being located in the cytoplasm.

EXAMPLE 6

Preparation of a Polyclonal Antibody Directed Against the Extracellular Loops (PEP1, PEP2 and PEP4) and Against an Intracellular Loop (PEP3) of ZnT-8

The peptides corresponding to the epitopes having the sequences SEQ ID NO. 7: PEP1: HIAGSLAVVTDAAHLL; SEQ ID NO. 8: PEP2: CERLLYPDYQIQATV; SEQ ID NO. 9: PEP3: CLGHNHKEVQANASVR; and SEQ ID NO. 10: PEP4: YFKPEYKIADPIC were solid-phase synthesized according to the method originally described by Merrifield et al. (*J. Am. Chem. Soc.,* 1964, 85: 2149-) (1946), purified and conjugated to a carrier protein (albumin, for example). The conjugated peptides were injected into rabbits according to the following immunization protocol:

D0: first immunization; D14: second immunization; D28: third immunization; D38: verification of the specificity; D56: fourth immunization; D66 and D80: recovery of serum. The serum can be used directly or after purification on a protein A column with elution in acidic medium. These operations were carried out using the client's material and requirements, by the company Eurogentec SA, Belgium.

EXAMPLE 7

Fluorescent Labeling of the Antibody Obtained in Example 6

The antibody is purified by affinity chromatography on a protein G column (Pharmacia). The column (1 ml), equilibrated with a 10 mM sodium phosphate buffer containing 0.15 M NaCl, pH 7.4, is loaded with 5 ml of serum and then washed with 20 ml of the same buffer in order to elute the unbound proteins. The antibody is then detached with a 0.1M glycine-HCl solution, pH 2.5, and then neutralized with 40 µl of 2M Tris-HCl buffer, pH 10.0.

2 mg of antibody are diluted in 1 ml of phosphate buffer, pH 8.0. A solution of NHS-FITC (SIGMA; 1 mg/ml in DMSO) is prepared extemporaneously. 75 µl of the NHS-FITC solution is mixed with the antibody solution and the mixture is then incubated at ambient temperature for 45 minutes. The labeled antibody is purified on a PD-10 column (PHARMACIA) in the following way: the column is washed with 30 ml of PBS, loaded with 1 ml of the solution of labeled antibody to be purified, and then with 5 ml of PBS, and 2 ml fractions are subsequently collected; the second fraction containing the labeled antibody is conserved.

BIBLIOGRAPHIC REFERENCES

1. Soria B.: In-vitro differentiation of pancreatic beta-cells. Differentiation 2001; 68: 205-19.
2. Gores P F, Sutherland D E. Pancreatic islet transplantation: is purification necessary? Am. J. Surg. 1993; 166: 538-42.
3. Bloc A, Cens T, Cruz H, Dunant Y. Zinc-induced changes in ionic currents of clonal rat pancreatic-cells: activation of ATP-sensitive K+ channels. J. Physiol. 2000; 529 Pt 3: 723-34.
4. Meyer K, Irminger J C, Moss L G, de Vargas L M, Oberholzer J, Bosco D, et. al.: Sorting human beta-cells consequent to targeted expression of green fluorescent protein. Diabetes 1998; 47: 1974-7.
5. Giordano C, Stassi G, Todaro M, Richiusa P, Giordano M, Mattina A, et al.: Autofluorescence-activated sorting of human single beta cells and endocrine non-beta cells after enzymatic islet dissociation. Transplant Proc; 1994; 26: 651-2.
6. Lukowiak B, Vandewalle B, Riachy R, Kerr-Conte J, Gmyr V, Belaich S, et al.: Identification and purification of functional human beta-cells by a new specific zinc fluorescent probe. J. Histochem. Cytochem. 2001; 49: 519-28.
7. Shiroi A, Yoshikawa M, Yokota H, Fukui H, Ishizaka S, Tatsumi K, et al.: Identification of Insulin-Producing Cells Derived from Embryonic Stem Cells by Zinc-Chelating Dithizone. Stem Cells 2002; 20: 284-292.
8. Jiao L, Gray D W, Gohde W, Flynn G J, Morris P J. In vitro staining of islets of Langerhans for fluorescence-activated cell sorting. Transplantation 1991; 52: 450-2.
9. Kallan A A, Roep B O, Arden S D, Hutton J C, de Vries R R: Beta-cell reactive T-cell clones from type I diabetes patients are not beta cell specific and recognize multiple antigens. J. Autoimmun. 1995; 8: 887-99.
10. Zalewski P D, Millard S H, Forbes I J, Kapaniris O, Slavotinek A, Betts W H et al.: Video image analysis of labile zinc in viable pancreatic islet cells using a specific fluorescent probe for zinc. J. Histochem. Cytochem. 1994; 42: 877-84.
11. Easom R A. Beta-granule transport and exocytosis. Semin. Cell. Dev. Biol. 2000; 11: 253-66.
12. Palmiter R D, Findley S D. Cloning and functional characterization of a mammalian zinc transporter that confers resistance to zinc. Embo J. 1995; 14: 639-49.
13. Sambrook J, Russell D W. (2000) Molecular Cloning. A Laboratory Manual, Cold Spring Harbor Laboratory Press.
14. Bloc A et al., J Physiol. 2000, Dec. 15; 529 Pt 3: 723-34).

The invention claimed is:

1. A monoclonal or polyclonal antibody selected from the group consisting of a chimeric antibody and a humanized antibody,
wherein
the antibody specifically recognizes the epitope of SEQ ID NO. 8.

2. The antibody of claim 1, which is a chimeric antibody.

3. The antibody of claim 1, which is a humanized antibody.

4. The antibody of claim 1, which is in the form of an immunoconjugate.

5. A method of isolating islets of Langerhans or beta cells, comprising:
bringing the cells of a biological sample liable to contain islets of Langerhans or beta cells into contact with a monoclonal or polyclonal antibody specific according to claim 1,
detecting the islets of Langerhans or beta cells labeled with the antibody, and
isolating the labeled islets of Langerhans or beta cells.

6. A method of visualizing differentiating stem cells, comprising
bringing the cells of a biological sample liable to contain stem cells undergoing differentiation into contact with a monoclonal or polyclonal antibody according to claim 1,
detecting the stem cells labeled with the antibody, and
visualizing the labeled stem cells.

7. The method as claimed in claim 6, further comprising isolating the labeled cells.

8. A method for detecting islets of Langerhans or beta cells, comprising:
bringing islets of Langerhans or beta cells into contact with a labeled monoclonal or polyclonal antibody according to claim 1, and
detecting the islets of Langerhans or beta cells labeled with the antibody.

* * * * *